US00PP26034P3

(12) United States Plant Patent
Nixon et al.

(10) Patent No.: US PP26,034 P3
(45) Date of Patent: Nov. 3, 2015

(54) APRICOT TREE NAMED 'MAC12/45'

(50) Latin Name: *Prunus armeniaca*
Varietal Denomination: Mac12/45

(71) Applicant: The New Zealand Institute for Plant and Food Research Limited, Auckland (NZ)

(72) Inventors: Arlene E. Nixon, Alexandra (NZ); Michael T. Malone, Havelock North (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 190 days.

(21) Appl. No.: 13/987,025

(22) Filed: Jun. 26, 2013

(65) Prior Publication Data

US 2013/0347154 P1 Dec. 26, 2013

Related U.S. Application Data

(60) Provisional application No. 61/664,158, filed on Jun. 26, 2012.

(51) Int. Cl.
*A01H 5/08* (2006.01)

(52) U.S. Cl.
USPC ..... Plt./186
CPC ..... *A01H 5/0843* (2013.01)

(58) Field of Classification Search
USPC ..... Plt./186
See application file for complete search history.

*Primary Examiner* — Susan McCormick Ewoldt
(74) *Attorney, Agent, or Firm* — Lathrop & Gage LLP

(57) ABSTRACT

A new and distinct apricot variety is described. The variety results from selection among a population of seedlings derived from controlled crossing of the varieties 'Bhart' (not patented), marketed as Orangered™, and an unreleased selection (not patented) which was the result of crossing 'Cluthagold' (not patented) and 'Late Moorpark' (not patented). The new variety is distinguished from others by the deep rose over color of the mature fruit accompanied by deep orange colored firm flesh with high soluble solids content. Fruit of 'Mac12/45' matures in early February in Otago, New Zealand and is notably precocious, fruiting in the second year after planting in Otago, New Zealand.

3 Drawing Sheets

Genus and species of plant claimed: *Prunus armeniaca.*
Variety denomination: 'Mac12/45'.

BACKGROUND TO THE INVENTION

Seedlings obtained from the deliberate crossing of 'Bhart' (not patented) (female parent), marketed as Orangered™, and an unreleased selection (not patented) (male parent) resulting from crossing 'Cluthagold' (not patented) and 'Late Moorpark' (not patented), in September 2003, were planted out at Clyde, Otago New Zealand, where the cross was also conducted. In February 2009, 'Mac12/45' was identified as having potential as a new variety. Later in 2009, 'Mac12/45' was asexually propagated from bud wood taken at Clyde and budded at Hawkes Bay 'Golden Queen' (not patented) peach seedlings, the standard apricot rootstock in New Zealand. The resulting trees were planted out at Clyde in the Southern Hemisphere winter of 2010, and were subsequently found to be true to type demonstrating that the characteristics of the new variety, 'Mac12/45', are stable and transmitted without change through succeeding generations.

SUMMARY OF THE INVENTION

'Mac12/45' is characterized by large fruit (100-120 g) with a deep rose overcolor, at maturity, deep orange colored firm flesh and high soluble solids content which mature in early February in Otago, New Zealand. 'Mac12/45' is distinguished from a number of varieties by the following characteristics:

When grown at Clyde, 'Mac12/45' is harvested one week earlier than 'F168' (U.S. Plant Pat. No. 16,071) (also known as 'Larclyd', marketed as Genevieve) and is orange in color with a solid flush of deep rose overcolor as compared with 'F168' which is yellow green in color with a speckled red overcolor.

The flesh of 'Mac12/45' is much finer in texture and firmer than that of 'F194' (U.S. Plant Pat. No. 16,119) (also known as 'Southern Cross').

Mac12/45 differs from its parent 'Bhart' as it is harvested approximately one month later than 'Bhart' when grown at Clyde.

The other parent, an unreleased seedling can be distinguished from Mac12/45 on fruit skin color at harvest maturity. Mac 12/45 has an orange background color and solid red blush overcolor at fruit maturity whereas the seedling parent had yellow green to pale orange background color and some speckling but no distinct block of blush color.

Mac 12/45 differs from Mac12/54 (U.S. Ser. No. 13/987,024) as Mac 12/45 is more precocious than Mac 12/54. Mac12/45 also has less intense fruit flavour than its sibling Mac 12/54.

BRIEF DESCRIPTION OF THE DRAWINGS

The accompanying photographs show typical specimens of the plant, fruit, and leaves of the new variety as depicted in colors as nearly true as is reasonably possible to make the same in color illustrations of this character.

DETAILED DESCRIPTION

Figure 1:
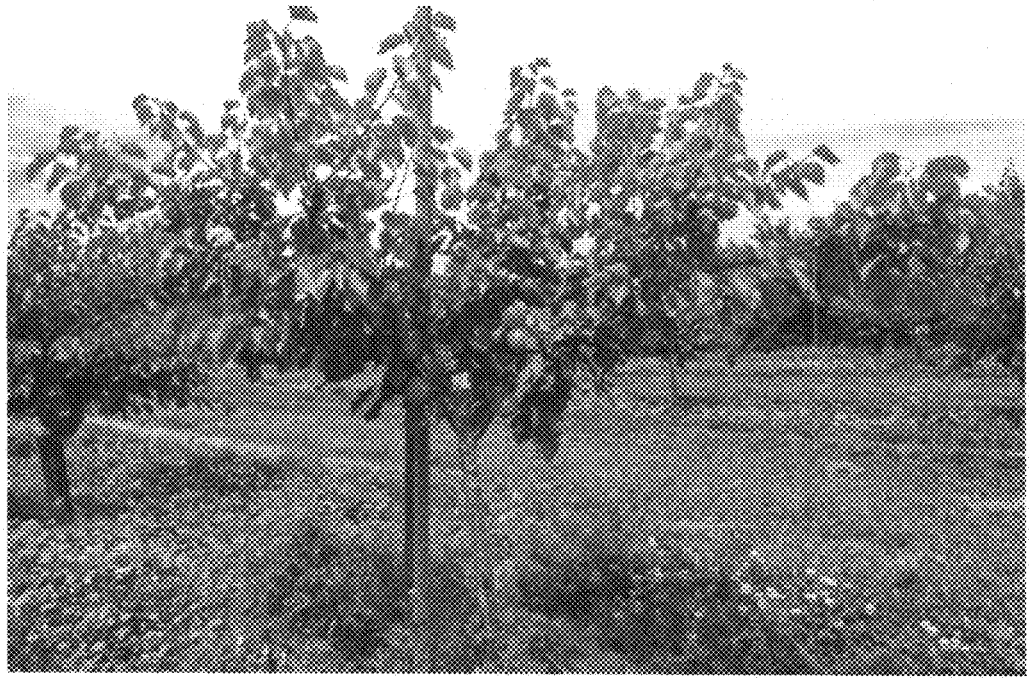
FIG. 1 shows a young 'Mac12/45' tree, approximately three years old, with fruit.
Figure 2:
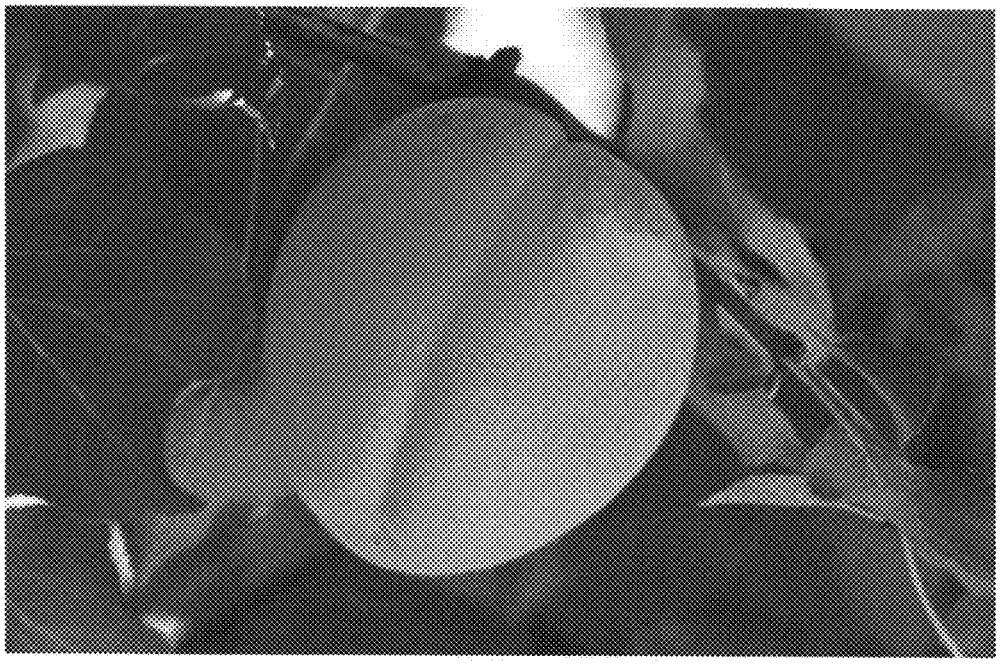
FIG. 2 shows a 'Mac12/45' fruit on the tree.
Figure 3:
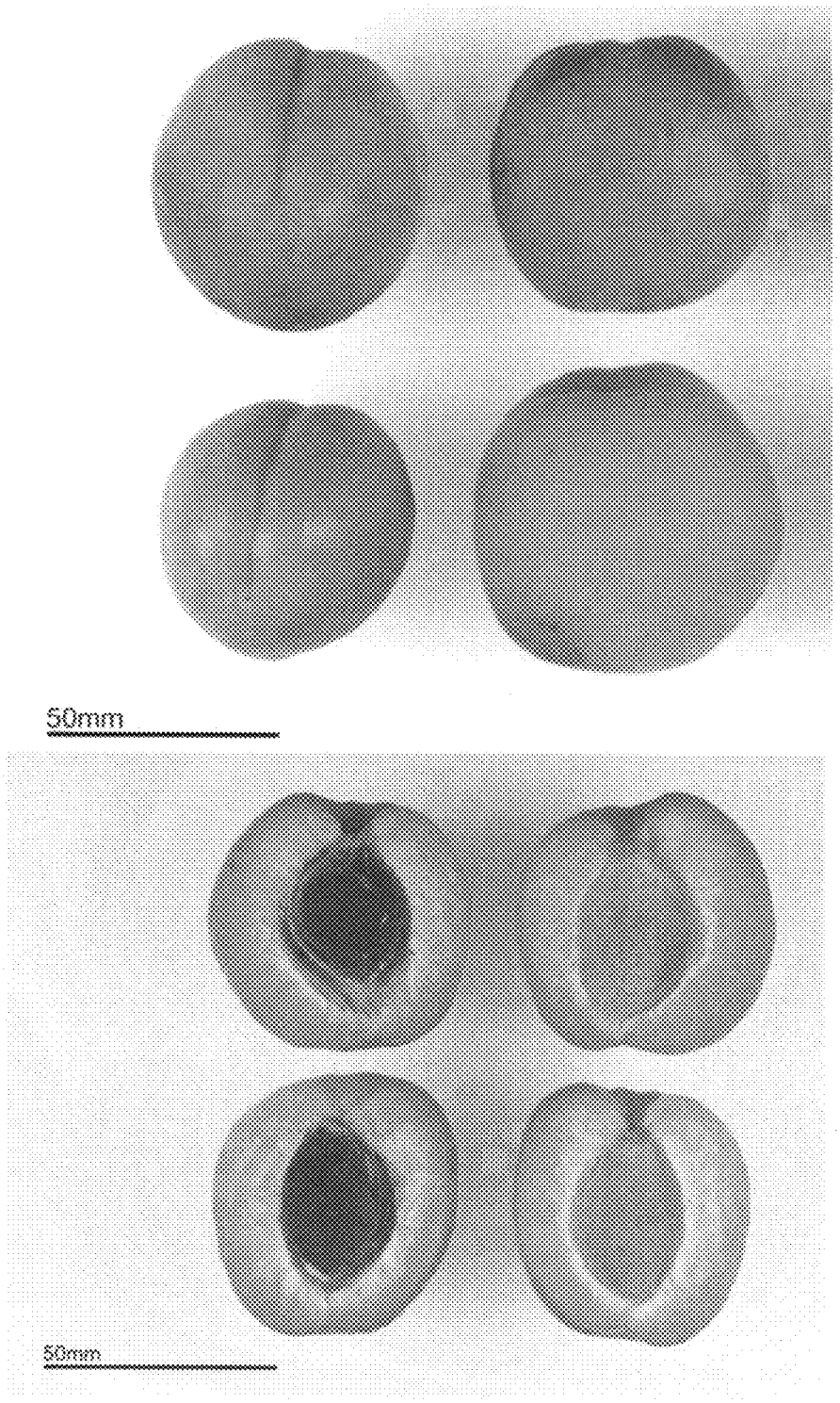
FIG. 3 shows a 'Mac12/45' fruit (top) whole and (bottom) longitudinal section.

The following is a brief description of the new variety with color terminology in accordance with The Royal Horticultural Society Colour Charts (R.H.S.C.C.) 2001 edition. The specimens described were grown at Clyde, New Zealand. The observations were made over the 2012-2013 seasons on 5 year old mature trees.

Tree: Medium vigour with an upright to spreading habit with a medium degree of branching. 'Mac12/45' scions are compatible on peach seedlings ('Golden Queen') rootstocks. Tree health is considered to be good under Central Otago conditions in New Zealand.

Trunk: Average circumference of a mature trunk, approximately 30 cm from the graft union was 327 mm. Trunk color was observed to be near grey orange 166A, with a reticulate bark texture, and a medium density distribution of near greyed yellow 161C oblanceolate lenticels which averaged approximately 4.0 mm long and 1.0 mm wide.

One-year-old shoot: Observed in winter, were observed to be near greyed orange 166A in color with near greyed orange 166A, medium sized bud supports which averaged approximately 5.5 mm in diameter and 4.9 mm in height. Dormant buds were observed to be ovate, moderately elongated, near brown 200A in color and approximately 5.5 mm long and 2.2 mm wide.

Leaves: The leaves examined were fully expanded and harvested from the central third of growing shoots in summer. The overall shape of the leaves was observed to be broad ovate with an acuminate tip approximately 8.6 mm long, a truncate base and serrate margins with medium undulation. Leaves are arranged alternatively and averaged 83.5 mm long and 79.1 mm wide. The color of the upperside was a medium intensity matte near green 137A and, the color of the underside was near green 137B. The venation pattern of the leaf was reticulate and the color of the venation was near yellow green 145C.

Petiole: The average petiole length of fully expanded leaves was 33.3 mm and 1.7 mm in diameter. The upperside of the petioles had a medium anthocyanin coloration of near purple N77A while the underside was near yellow green 145C. Petioles were observed to have between two and three medium sized nectaries close to the leaf base which had a diameter of 1.4 mm.

Flowers: Observations were made at full bloom unless otherwise stated. Bud burst was recorded in early to mid September (approximately 11$^{th}$ September), with full bloom, 90% of flowers open, occurring mid September (approximately 18$^{th}$ September). Flowers were medium sized, the average diameter of an open flower with petals pressed flat was 33 mm and distributed approximately equally on spurs and one-year-old shoots.

Corolla: Five overlapping petals per flower, with an average length of 11.9 mm (excluding claw) and an average width of 11.2 mm and a 1.7 mm claw. The petals shape (excluding claw) was broad elliptic with a smooth margin with slight undulation. Petals were near white, N155D at full bloom.

Stamens: An average of 30 per flower. Filaments were translucent white in color, and an average of 8.5 mm long, with near yellow orange 12 C anthers and near greyed yellow 162A pollen. Anthers were on average 1.2 mm long and 0.8 mm wide.

Carpel: Pistals were on average approximately 10.6 mm and colored near yellow 11D. The stigma sat at approximately the same level as the anthers.

Pedicel: Average approximately 6.1 mm long and 4.5 mm wide.

Calyx: Five sepals per flower, an average length of 4.8 mm and width of 2.8 mm with a right angle apex and an undulating margin. Colored near purple N77.

Fruit: Fruit at horticultural maturity were medium sized an observed to be on average 83.3 g, with an average height of 49.0 mm, average lateral width of 50.6 mm, and average ventral width of 44.3 mm. Mac12/45 fruit were symmetric and were circular in lateral view and elliptic in ventral view with a slightly sunken suture and a rounded apex. The stalk cavity was medium in depth, approximately 3.1 mm deep. The skin surface was smooth with minimal pubescence, weak gloss, a mid orange background color, and approximately 25-50% overcolor colored near orange red N34A made up of a solid flush. The flesh color was near orange N25D and near orange N25D in the stone cavity with some whiteness around the stone. The flesh texture was fine with medium firmness, a weak adherence to the stone and average soluble solids of approximately 18.3%.

Stone: Observations made on dry stones unless otherwise stated. Stones were obovate in shape, lateral view, with a moderately obtuse apex, and truncate base. Stones were on average approximately 23.2 mm long, with an average lateral width of 18.5 mm. The stone was colored near grey brown N199B.

Harvest timing: Fruit begin ripening late in the season, approximately 12$^{th}$-16$^{th}$ February in Clyde, New Zealand.

Use: Fresh eating.

Pest and disease: 'Mac12/45' has no known particular tolerances or susceptibilities to pests and diseases associated with apricot trees.

The invention claimed is:

1. A new and distinct apricot plant substantially as herein illustrated and described.

* * * * *